US010166148B2

(12) United States Patent
Dunn

(10) Patent No.: US 10,166,148 B2
(45) Date of Patent: Jan. 1, 2019

(54) SURGICAL CAVITY DRAINAGE AND CLOSURE SYSTEM

(71) Applicant: University of Massachusetts, Boston, MA (US)

(72) Inventor: Raymond Dunn, Shrewsbury, MA (US)

(73) Assignee: University of Massachusetts, Boston, MA (US)

( * ) Notice: Subject to any disclaimer, the term of this patent is extended or adjusted under 35 U.S.C. 154(b) by 172 days.

(21) Appl. No.: 13/675,736

(22) Filed: Nov. 13, 2012

(65) Prior Publication Data

US 2013/0274717 A1 Oct. 17, 2013
US 2016/0317792 A9 Nov. 3, 2016

Related U.S. Application Data

(63) Continuation-in-part of application No. PCT/US2012/033608, filed on Apr. 13, 2012.
(Continued)

(51) Int. Cl.
*A61M 27/00* (2006.01)
*A61F 13/02* (2006.01)
(Continued)

(52) U.S. Cl.
CPC ...... *A61F 13/0216* (2013.01); *A61B 17/0401* (2013.01); *A61F 13/00068* (2013.01);
(Continued)

(58) Field of Classification Search
USPC .......................................................... 604/541
See application file for complete search history.

(56) References Cited

U.S. PATENT DOCUMENTS 4,257,422 A 3/1981 Duncan
4,429,693 A * 2/1984 Blake .................. A61M 1/0011
600/578

(Continued)

FOREIGN PATENT DOCUMENTS

WO 2006119256 A2 11/2006
WO 2007143179 A2 12/2007

OTHER PUBLICATIONS

Grabow, Niles, et al., "A Biodegradable Slotted Tube Stent Based on Poly(L-lactide) and Poly(4-hydroxybutyrate) for Rapid Balloon-Expansion", Annals of Biomedical Engineering, vol. 35, No. 12, Dec. 2007, pp. 2031-2038.
(Continued)

*Primary Examiner* — Tatyana Zalukaeva
*Assistant Examiner* — Guy K Townsend
(74) *Attorney, Agent, or Firm* — McCarter & English, LLP; Thomas O. Hoover

(57) ABSTRACT

A surgical drain device includes a matrix of biodegradable polymer material and a plurality of drain tubes attached to the matrix. The device is implanted within a surgical wound to treat the presence of seromas, for example, and is used to promote drainage, tissue adhesion, and wound closure. The drain tubes converge into a common collection tube that leads wound fluid outside the body under gravity feed or negative pressure applied to the collection tube. The matrix contains an array of apertures that allow tissue contact across the device. A preferred embodiment comprises a tissue anchoring system including anchor elements such as hooks or barbs. The device can be used with a negative pressure system to further improve the drainage band can also be used with a wound dressing. The device and systems containing the device are particularly useful to promote the healing of surgical wounds from abdominal surgery.

42 Claims, 10 Drawing Sheets

Related U.S. Application Data

(60) Provisional application No. 61/475,945, filed on Apr. 15, 2011.

(51) Int. Cl.
    *A61F 13/14* (2006.01)
    *A61B 17/04* (2006.01)
    *A61M 1/00* (2006.01)
    *A61F 13/00* (2006.01)

(52) U.S. Cl.
    CPC ......... *A61F 13/148* (2013.01); *A61M 1/0023* (2013.01); *A61M 1/0039* (2013.01); *A61M 1/0088* (2013.01); *A61M 27/00* (2013.01); *A61F 13/00072* (2013.01); *A61F 13/0203* (2013.01); *A61F 2013/0054* (2013.01); *A61F 2013/00174* (2013.01); *A61F 2013/00412* (2013.01); *A61F 2013/00536* (2013.01); *A61M 1/008* (2013.01); *A61M 2027/004* (2013.01); *A61M 2205/3334* (2013.01); *A61M 2205/50* (2013.01); *A61M 2205/52* (2013.01)

(56) References Cited

U.S. PATENT DOCUMENTS

| | | | |
|---|---|---|---|
| 4,579,555 A | 4/1986 | Russo | |
| 4,608,041 A | 8/1986 | Nielsen | |
| 4,781,678 A | 11/1988 | de Couet et al. | |
| 5,116,310 A | 5/1992 | Seder et al. | |
| 5,549,579 A | 8/1996 | Batdorf et al. | |
| 5,628,735 A | 5/1997 | Skow | |
| 5,636,643 A * | 6/1997 | Argenta | A61M 1/0088 128/897 |
| 6,099,513 A | 8/2000 | Spehalski | |
| 6,478,789 B1 | 11/2002 | Spehalski et al. | |
| 6,641,575 B1* | 11/2003 | Lonky | A61B 17/00234 600/210 |
| 6,685,681 B2* | 2/2004 | Lockwood | A61M 1/0058 502/43 |
| 6,814,079 B2* | 11/2004 | Heaton | A61F 13/023 128/897 |
| 7,125,402 B1 | 10/2006 | Yarger | |
| 7,182,758 B2 | 2/2007 | McCraw | |
| 7,216,651 B2* | 5/2007 | Argenta | A61M 1/0088 128/897 |
| 7,322,971 B2 | 1/2008 | Shehada | |
| 7,351,250 B2 | 4/2008 | Zamierowski | |
| 7,381,211 B2 | 6/2008 | Zamierowski | |
| 7,381,859 B2 | 6/2008 | Hunt et al. | |
| 7,402,620 B2 | 7/2008 | McGhee | |
| 7,410,495 B2 | 8/2008 | Zamierowski | |
| 7,413,570 B2 | 8/2008 | Zamierowski | |
| 7,413,571 B2 | 8/2008 | Zamierowski | |
| 7,658,749 B2 | 2/2010 | Wittmann | |
| 7,699,831 B2 | 4/2010 | Bengtson et al. | |
| 8,079,991 B2 | 12/2011 | Watson | |
| 8,777,911 B2* | 7/2014 | Heagle | A61F 13/02 604/317 |
| 2001/0029956 A1 | 10/2001 | Argenta et al. | |
| 2001/0044637 A1 | 11/2001 | Jacobs et al. | |
| 2002/0077661 A1 | 6/2002 | Saadat | |
| 2002/0150720 A1 | 10/2002 | Howard et al. | |
| 2002/0161346 A1* | 10/2002 | Lockwood | A61M 1/0058 604/315 |
| 2003/0109855 A1 | 6/2003 | Solem et al. | |
| 2005/0065484 A1 | 3/2005 | Watson | |
| 2005/0107756 A1* | 5/2005 | McCraw | A61M 1/0088 604/317 |
| 2005/0240220 A1 | 10/2005 | Zamierowski | |
| 2006/0041247 A1 | 2/2006 | Petrosenko et al. | |
| 2007/0021760 A1* | 1/2007 | Kelleher | A61B 17/0469 606/153 |
| 2007/0021779 A1 | 1/2007 | Garvin et al. | |
| 2007/0027414 A1 | 2/2007 | Hoffman et al. | |
| 2007/0032763 A1* | 2/2007 | Vogel | A61M 1/0031 604/305 |
| 2007/0249999 A1* | 10/2007 | Sklar | A61B 18/1815 604/101.05 |
| 2007/0276316 A1 | 11/2007 | Haffner et al. | |
| 2008/0033324 A1 | 2/2008 | Cornet et al. | |
| 2008/0033401 A1* | 2/2008 | Watson | A61F 13/0203 604/543 |
| 2008/0064953 A1 | 3/2008 | Falco et al. | |
| 2008/0097601 A1 | 4/2008 | Codori-Hurff et al. | |
| 2008/0114277 A1* | 5/2008 | Ambrosio | A61F 13/00987 602/46 |
| 2008/0200950 A1* | 8/2008 | Wohlert | A61B 17/064 606/221 |
| 2008/0300625 A1 | 12/2008 | Zamierowski | |
| 2009/0012482 A1* | 1/2009 | Pinto | A61F 13/00029 604/313 |
| 2009/0069904 A1* | 3/2009 | Picha | A61F 2/18 623/23.72 |
| 2010/0069886 A1 | 3/2010 | Wilkes | |
| 2010/0160719 A1* | 6/2010 | Kassab | A61M 25/0147 600/37 |
| 2010/0179516 A1 | 7/2010 | Bengtson et al. | |
| 2010/0234716 A1* | 9/2010 | Engel | A61B 5/02055 600/391 |
| 2010/0274177 A1 | 10/2010 | Rybski et al. | |
| 2010/0292717 A1 | 11/2010 | Petter-Puchner et al. | |
| 2011/0028898 A1* | 2/2011 | Clark, III | A61B 18/1477 604/151 |
| 2011/0071484 A1 | 3/2011 | Song | |
| 2011/0130730 A1 | 6/2011 | Hartwell et al. | |
| 2011/0301556 A1* | 12/2011 | Lichtenstein | A61F 13/00068 604/319 |
| 2012/0041403 A1* | 2/2012 | Bennett | A61F 13/00068 604/319 |
| 2012/0116334 A1* | 5/2012 | Albert | A61F 13/02 604/319 |
| 2012/0165725 A1* | 6/2012 | Chomas | A61M 1/008 604/22 |
| 2013/0203012 A1* | 8/2013 | Walker | A61C 17/043 433/92 |
| 2013/0274717 A1* | 10/2013 | Dunn | A61M 27/00 604/541 |
| 2013/0281784 A1* | 10/2013 | Ray | A61B 1/32 600/205 |
| 2014/0039468 A1* | 2/2014 | Dunn | A61M 27/00 604/541 |

OTHER PUBLICATIONS

Kontakis, George M., et al., "Bioabsorbable Materials in Orthopaedics", Acta Orthopaedica Belgica, vol. 73, Feb. 2007, pp. 159-169.

International Search Report and Written Opinion of the International Searching Authority for International Application No. PCT/US13/69916 dated Mar. 27, 2014.

International Preliminary Report on Patentability by the International Bureau of WIPO for international application No. PCT/US13/69916 dated May 19, 2015.

Supplementary Partial European Search Report by the European Patent Office for European Application No. EP 12772030.8 dated Jun. 1, 2015.

Extended European Search Report by European Patent Office for European Application No. EP 12772030.8 dated Sep. 22, 2015.

* cited by examiner

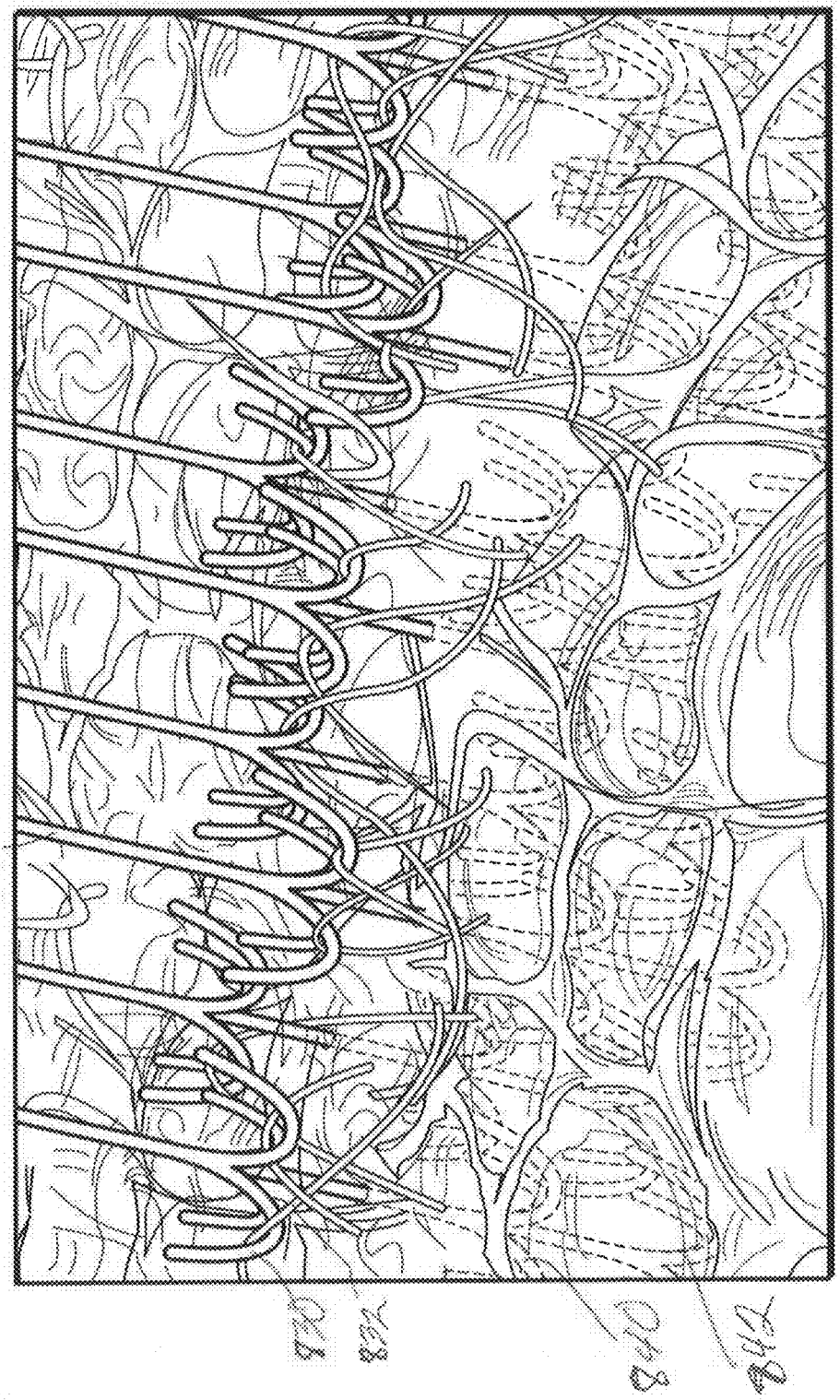

SURGICAL CAVITY DRAINAGE AND CLOSURE SYSTEM

CROSS REFERENCE TO RELATED APPLICATION

This application is a continuation-in-part application of PCT/US2012/033608 filed on Apr. 13, 2012, which claims the priority to U.S. Application No. 61/475,945, filed Apr. 15, 2011, the entire contents of the above applications being incorporated herein by reference.

BACKGROUND OF THE INVENTION

A variety of systems have been proposed for draining surgical wounds. The efficacy of such systems has been limited, however, especially for larger surgical spaces or those in which certain characteristics, such as motion or shape, or certain physiological characteristics, such as lymphatic drainage or low protein exist. Seroma is a frequent complication following surgery, and can occur when a large number of capillaries have been severed, allowing plasma to leak from the blood and lymphatic circulation. Surgical wounds that can lead to seroma formation include wounds resulting from surgery involving an abdominal flap, such as abdominoplasty surgery, breast reconstruction surgery, panniculectomy, and ventral hernia repair.

Available surgical drain devices suffer from several deficiencies, particularly when applied following abdominal flap surgery. They fail to drain fluid adequately, are prone to clogging, and fail to promote tissue adhesion within the wound. Thus, there remains a need to develop improved treatments for surgical wounds. The need is particularly acute in abdominal surgery, such as for the prevention and treatment of seromas, but also for any surgical wound predisposed to conditions of excess fluid drainage or tissue motion, or benefitting from tissue adhesion needs, such as pressure ulcers or wounds resulting from a tissue harvesting procedure.

SUMMARY OF THE INVENTION

The invention provides a surgical drain device for the prevention and treatment of seromas as well as for general use in promoting drainage of surgical wounds and wound closure. The drain device includes a plurality of drain tubes disposed on a substrate termed an "adhesion matrix," which is designed to promote tissue adhesion within the seroma or wound space. The adhesion matrix has a conformable configuration and is made of a compliant material having planar surfaces that can curve to adapt to the shape of the wound space.

In a preferred embodiment, the adhesion matrix contains a plurality of apertures, or gaps in the matrix material, which allow tissue contact across the matrix, so as to promote adhesion and wound closure. Thus, a tissue surface on a first side of the matrix can directly contact a tissue surface on a second, or opposite, side of the matrix to promote rapid healing and stabilization of the wound. The number, size and distribution of the apertures extending through the matrix can be selected based on the geometry of the wound. For abdominal wounds, for example, the drain tubes can be positioned in a fan shaped array with a plurality of three or more tubes extending from a manifold. The matrix and/or the tubing can be cut or shaped by the user to conform to the shape of the wound. The matrix can also be used as a medication carrier to assist in the administration of a drug to a patient. The matrix can optionally include a layer of adhesive on at least a portion of any of its surfaces. The drain tubes can be removed from the device once drainage flow is sufficiently reduced, and the adhesion matrix can remain within the body, where it is degraded and absorbed over time, remaining in place to optimize tissue healing. The matrix can comprise a porous biodegradable polymer material. As the plurality of tubes extend from a single exit site into the wound with spaced apart distal ends, a user can readily remove all the tubes simultaneously from the wound.

The surgical drain device can include a tissue anchoring system, whereby the device is mechanically attached to surrounding tissues by an array of surface barbs or hooks. These surface structures can be located on any exposed surface of the adhesion matrix. When the device is implanted, the surrounding tissues can be pressed against the barbs or hooks to embed them within the tissue and anchor the device. The use of surface barbs or hooks can be used in combination with a surgical adhesive, providing a much stronger bond between tissue layers than the adhesive alone, and providing temporary adhesion while the adhesive sets. The structure of the hooks can have various forms depending on the tissue they are intended to bind. Longer hooks can be used for loosely bound tissues such as fat or connective tissue, while shorter hooks can be used for denser tissues such as muscle or fascia. Anchors with more rigid stems can be utilized to penetrate denser tissues. Preferred embodiments of the invention relate to tissue anchor devices that can be used for many applications such as attached the same or different types of connective tissues such as muscle, fat and/or fascia. Additional embodiments provide for the attachment of tissue to organs or the reattachment of cylindrical tissue structures such as nerves and tendons using tubular tissue anchor devices. Tubular tissue anchor connect separated or damaged structures using anchor elements extending from the interior surface.

The tissue anchor elements can be arranged with a sufficient areal density over the surface(s) of the device to connect the tissue structures with sufficient force to retain the structures in relative position for healing while having the ability to release from the tissue without causing additional damage to the tissue. Generally there can be 1-10 anchor elements per square millimeter for many applications that are distributed across the tissue contacting surface.

A preferred embodiment of the invention relates to methods of fabricating anchor elements for a tissue anchor device. Such methods relate to the manufacture of tissue anchor elements that have different anchor features to attach to different tissue types. The anchor elements can comprise sharpened barbs or fibers densely arrayed across a mesh surface, coated filaments or posts made with, or inserted into, or through a mesh material to form a composite structure. The tips or ends of the anchor elements can be shaped to promote adhesion.

Another aspect of the invention is a system for surgical wound drainage. The system includes the drain device described above together with a vacuum source, such as a pump, and a tube connecting the vacuum source to the drain tubes of the drain device. The system optionally also can include a fluid trap to collect drained fluid and a control unit to monitor and control the application of vacuum and the collection of fluid. Further components of the system can include a vacuum or pressure gauge, a flow meter, and a computer to monitor vacuum and flow and to regulate vacuum or flow.

Another aspect of the invention is a method for treating or preventing a seroma, or promoting the drainage or closure of a surgical wound. The method includes positioning the drain device described above into a seroma, or a surgical wound, such as a wound at risk of forming a seroma, and allowing the device to drain fluid from the wound for a period of time. The device can include surgical adhesive and/or barbs or hooks on its surface to create adhesion between tissue layers within the wound and to anchor the device in place. Drainage can be by gravity flow or can be vacuum assisted by attaching a vacuum source to the drain tubes of the device, using a manifold to merge the flow paths of the drain tubes to a common drain tube for collection. Negative pressure applied to the drain tubes can be used to hold the tissue layers above and below the device together until a surgical adhesive has set, or until the wound healing process binds the tissues together. The application of negative pressure further facilitates contact between tissue on opposite sides of the matrix through the apertures in the matrix to promote tissue adhesion. This improves the rate of healing while at the same time providing for drainage. Optionally, the drain tubes of the device can be removed from the body after drainage flow is reduced, thereby reducing the burden for resorption by the body. Removal of the drain tubes can be facilitated by the inclusion of drain tube channels, or drain tube release tabs, within the adhesion matrix. Release of the drain tubes is then accomplished by sliding the tubes out of the channels or appropriately maneuvering the drain tube assembly to break release tabs. The adhesion matrix is allowed to remain in the seroma or surgical wound where it is resorbed over time.

The flow rate from the drain tubes can be regulated by flow control elements. The flow rate can also be measured or the pressure of fluids can be measured by ultrasound devices or by other methods. The system can also be used in conjunction with wound dressings that can also be attached to a negative pressure source to remove fluids from the wound.

BRIEF DESCRIPTION OF THE DRAWINGS

FIGS. 5A-5D show representative embodiments having different mechanisms of attaching drain tubes to the polymer matrix. In FIG. 5A the drain tubes are encased within drain tube channels, and in FIG. 5B the drain tubes are attached via retaining structures. In FIG. 5C the drain tubes are glued onto the matrix, and in FIG. 5D the drain tubes are spot welded onto the matrix. FIGS. 5E and 5F show embodiments having different configurations of drain tubes within drain tube channels. FIG. 5G shows a drain tube embodiment having lateral apertures for collection of fluid.

FIG. 15 illustrates a tissue anchor with anchor elements positioned to connect at different depths of the device in accordance with preferred embodiments of the invention.

DETAILED DESCRIPTION OF THE INVENTION

The present invention provides a surgical drain device, system, and method that allow fluid to be drained from surgical wounds and promote the healing of the wound. Preferred embodiments are used to prevent or treat seromas, for example. The drain device features a set of drain tubes that are attached to a substrate, herein referred to as an adhesion matrix that is designed to promote adhesion of tissues within the wound or seroma and to encourage cellular infiltration into the device itself. The drain tubes are distributed across the adhesion matrix to promote even drainage across the device. To promote optimum drainage, the drain tubes can be uniformly distributed across the adhesion matrix. The drainage device can be left in place within the wound for a period of time, e.g., until fluid seepage diminishes, after which the drain tubes can be withdrawn from the device and removed from the patient without disturbing the adhesion matrix, which is left in place to biodegrade or become incorporated into the healing process. The device efficiently promotes the healing of even large area wounds such as those resulting from abdominal flap surgery.

Figure 1:
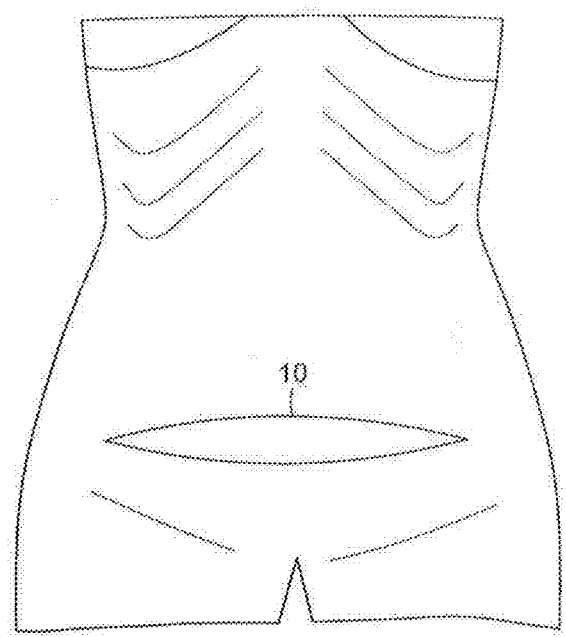
FIG. 1 shows a drawing of the abdomen of a patient who has an abdominal flap wound resulting from abdominal surgery.
Figure 2:
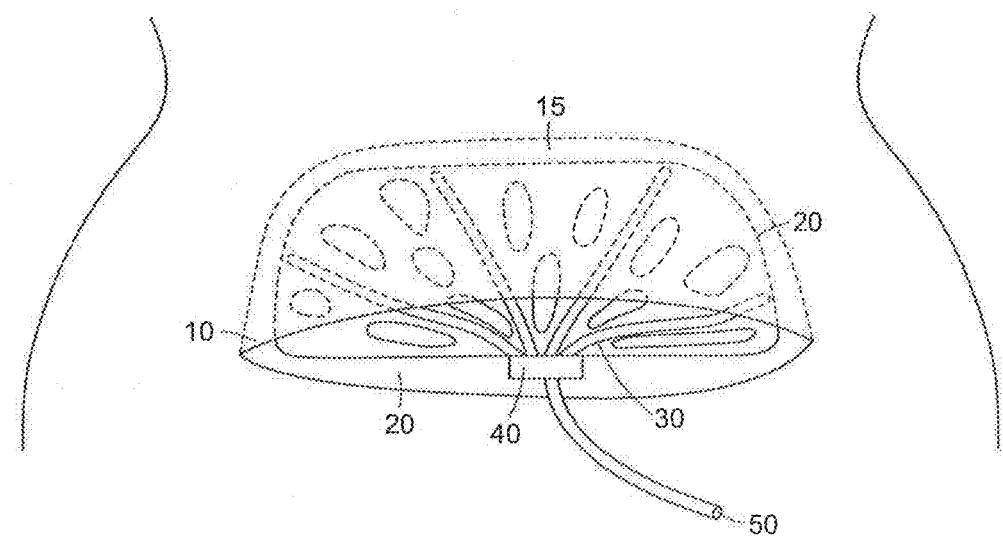
FIG. 2 shows a drawing of a surgical drain device according to the invention which has been inserted through an abdominal flap wound.

A surgical drain device according to the invention is inserted through an incision in the skin of a patient and placed within a wound formed during surgery. A first purpose is to drain fluid during the surgical procedure. The system can be left in place and to provide drainage for days or even weeks following surgery. The device can be used for the treatment of a seroma, e.g., to drain a seroma and thereby promote its healing, it can also be used to prevent seroma formation. For example, the drain device can be placed routinely into surgical incision areas immediately following surgery and used to drain the area and aid in the prevention of seroma formation. Alternatively, the device can be placed into a seroma that has already formed by opening the seroma and installing the device. The use of the drain device is understood to "prevent" seroma formation even if it merely reduces the likelihood of seroma formation. Similarly, the use of the drain device is understood to "treat" seroma formation even if it merely increases the likelihood that the seroma will heal. FIG. 1 shows an abdominoplasty or abdominal flap wound (10) in a patient resulting from abdominal surgery. FIG. 2 shows surgical drain device 20 inserted through abdominal flap wound 10 and into the space occupied by seroma 15.

The device according to the invention includes a number of removable drain tubes 30 attached at their proximal ends to manifold 40, which connects to a vacuum source through vacuum tubing 50. The drain device collects and removes fluid from the abdominal region or from the fluid space of a seroma through the drain tubes, which divert the fluid outside the patient through the aid of a vacuum source. The number of drain tubes can vary depending upon the needs of the device, including the amount of fluid to be drained and the size of the wound and shape of the device. Typically, the device will contain from 2 to about 20 drain tubes. In a preferred embodiment, the device contains preferably at least 3 tubes, and for larger areas such as the abdomen, for example, from about 5 to about 12 tubes.

The drain tubes can be fabricated from any biocompatible thermoplastic or thermoset material. Examples include surgical grade silicone rubber, polyurethane, polyamide, polyimide, PEEK (polyether ether ketone), polycarbonate, PMMA (polymethylmethacrylate), and polyvinylchloride. The drain tubes are intended to be removed after fluid build-up has reduced to a level that is stable without drainage. However, in an alternative embodiment, the drain tubes can be made of a biodegradable material and can be left in place. The drain tubes can be flexible so as to conform to the tissues surrounding the device and to accommodate movement of the patient without causing discomfort. The drain tubes can be open ended or close ended. In a preferred embodiment, the drain tubes are close ended and possess apertures or holes along their length for the uptake of fluid.

Figure 3:
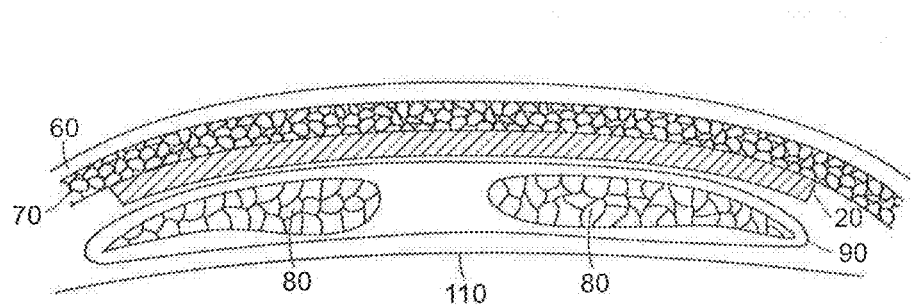
FIG. 3 shows a cross-sectional view of a surgical drain device according to the invention installed in the abdomen of a human patient between subcutaneous tissue and a layer of abdominal muscle.

FIG. 3 shows drain device 20 installed in the abdomen between subcutaneous tissue 70 and a layer of abdominal muscle 80 and associated fascia 90. While this position can be used following abdominal flap surgery, other anatomical locations of the device are also possible and are contemplated as suitable uses of the invention.

Figure 4:
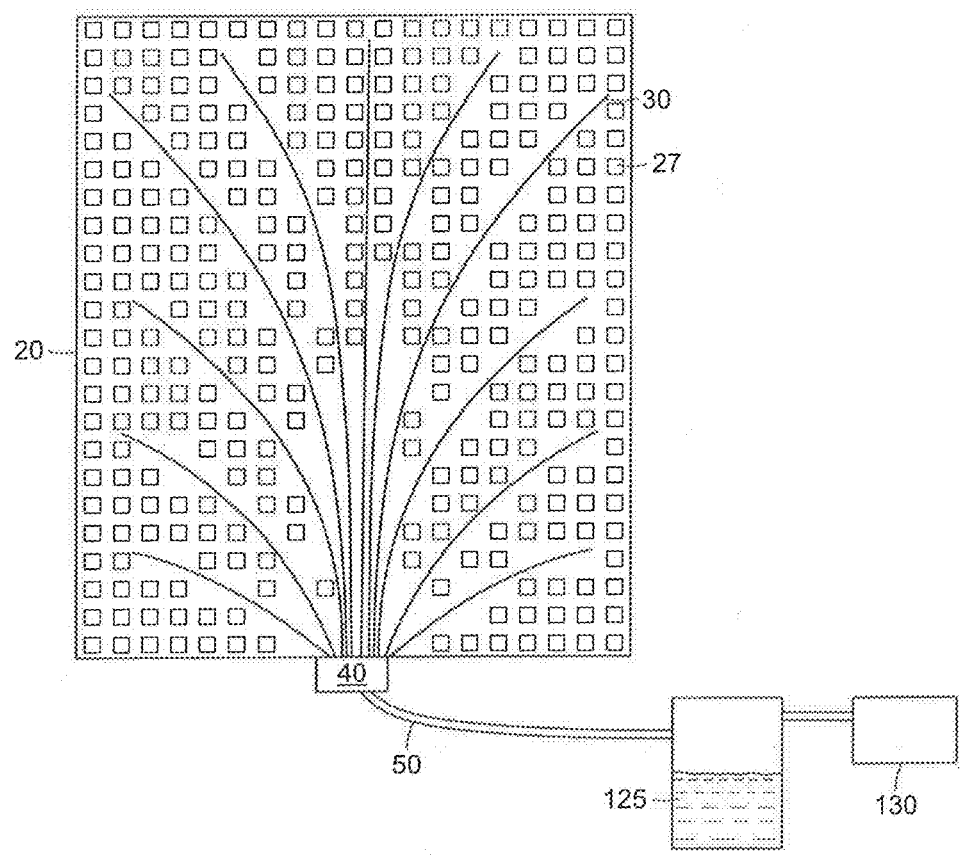
FIG. 4 is a schematic diagram of a surgical wound drainage system according to the invention.

FIG. 4 schematically depicts a system for drainage of a seroma through an abdominal flap wound. System 21 includes drain device 20, having a plurality of drain tubes 30 attached to adhesion matrix 25 and configured so as to drain the full extent of the seroma. The drain tubes are connected at their proximal ends to manifold 40, which is in turn connected through vacuum tubing 50 to a vacuum pump 130 or other vacuum source. Fluid 125 drained from the wound can be optionally accumulated in fluid trap 120. Vacuum pump or other vacuum source 130 can include one or more electronic devices, such as a microprocessor with memory and software, to monitor the vacuum level, pneumatic resistance, and/or fluid removal amount or rate. The electronic device(s) also can be used to control the operation of the system over time according to user-defined parameters, according to a preset program, or in response to data collected on vacuum, resistance, and/or fluid removal.

Figure 5A:
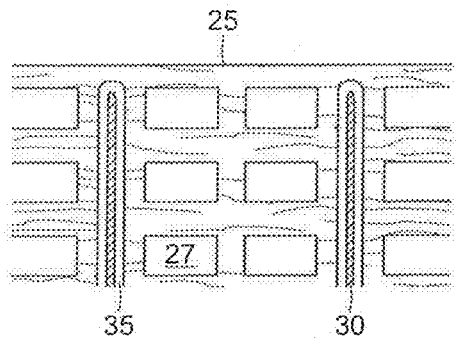
FIGS. 5A-5G are illustrations of embodiments of a surgical drain device according to the invention, depicting the disposition of drain tubes within the device and features of the drain tubes and polymer matrix.

FIGS. 5A-5G depict representative embodiments of a drain device according to the invention, showing several possible configurations of the drain tubes within the device. FIG. 5A shows an embodiment in which each drain tube 30 is disposed within a separate drain tube channel 35. The drain tube channels are embedded within or attached to the surface of adhesion matrix 25 and determine the orientation and distribution of the drain tubes within the device. In a preferred embodiment, the drain tube channels, and consequently the drain tubes, are evenly distributed across the surface area of the drain device, as shown in FIG. 4. These can extend in a generally radial distribution from one edge or region on the matrix to enable use of a single exit tube from the wound. However, the drain tubes can be unevenly distributed if desired, e.g., to increase the drainage capacity or rate from specific areas of the device. The use of drain tube channels ensures that the drain tubes remain in position within the patient and ensures that the drain tubes can be removed easily at the appropriate time, without disrupting the wound healing process. Drain tube channels require a mechanism to accept fluid and pass it on to the drain tubes within. Suitable mechanisms include using apertures or holes of any desired shape and distribution along the length of the channels (see, e.g., apertures 33 on channels 35 in FIG. 6D), and using a porous material to form the drain tube channels (see drain tube channels 35 in FIGS. 5E and 5F, constructed of a porous polymer matrix).

Figure 5B:
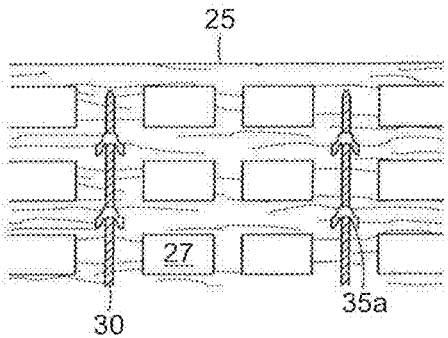
Figure 5C:
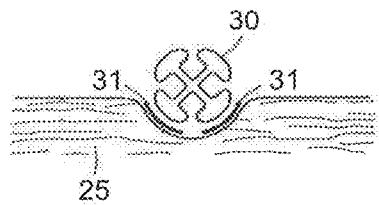
Figure 5D:
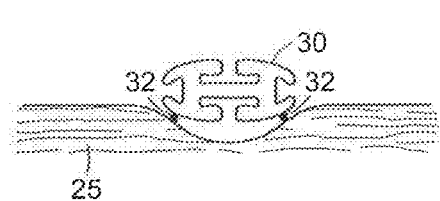

Several alternative embodiments are also contemplated which lack drain tube channels. FIG. 5B depicts the use of retaining structures 35a instead of channels in order to removably attach the drain tubes to the adhesion matrix, while allowing removal of the tubes by sliding or by breaking off the retaining structures. The retaining structures can have any form compatible with their function. FIG. 5C shows an embodiment in which drain tube 20 is held in place by layer of adhesive 31, and the tube is fitted within a depression on the surface of adhesion matrix 25. In the related embodiment shown in FIG. 5D, the drain tube is held in the matrix depression by spot welds or adhesion points 32, which can be broken through suitable manipulation to remove the tubes.

Figure 5E:
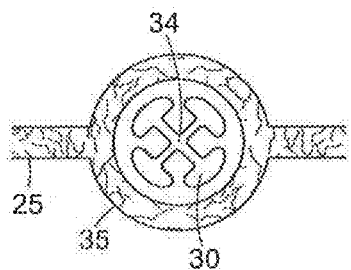
Figure 5F:
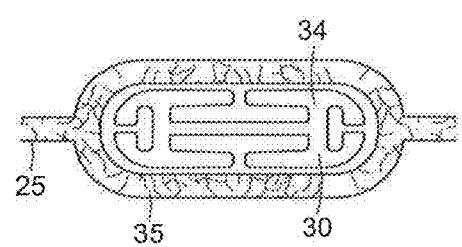

FIGS. 5E and 5F present cross-sectional views of a portion of the adhesion matrix 25 of an embodiment of a drain device according to the invention. The adhesion matrix contains regions for receiving drain tubes or can include one or more drain tube channels 35 which surrounds drain tubes 30, having lumen 34, through which seroma or other wound fluid is removed. A round Blake drain is depicted as the drain tube in FIG. 5E, and a flattened version in FIG. 5F. A variety of drain tube profile shapes are possible, including oval, elliptical, square, rectangular, triangular, flattened, compound (i.e., having 2 or more parallel lumens, interconnected or separated), or irregular. The drain tubes optionally can be coated with a lubricant on their outer surfaces to facilitate their removal from the channels.

Figure 5G:
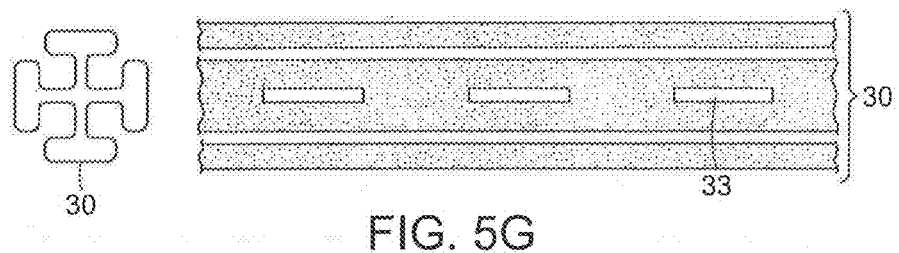

In a preferred embodiment the drain tubes possess openings or apertures 33 along their length to permit fluid to enter for drainage. FIG. 5G depicts one such embodiment. The relative surface area and distribution of such apertures can be chosen so as to regulate flow through the drain tubes. For example, pressure drop (i.e., loss of vacuum) along the length of the drain tubes can be compensated by increasing the open surface area or the density of apertures towards the distal end of the drain tubes. Drain tubes are preferred which have an aperture distribution that provides an essentially constant rate of fluid uptake along the length of the drain tubes (e.g., increasing aperture area towards the distal end), so that uniform drainage is obtained across the drain device.

Adhesion matrix 25 includes a plurality or matrix of apertures 27 which allow tissue contact through the drain device. Such tissue contact promotes wound healing and the sealing of capillaries, which is important for treating seromas or preventing their formation. In the drain device according to the present invention, the promotion of tissue contact works in combination with fluid drainage to promote wound healing. The adhesion matrix 25 and its drain tube channels 35 preferably are constructed of one or more biodegradable polymer materials and can be left within the wound, where they stabilize tissue infiltration and adhesion and thus promote the healing process. The size, shape, and distribution of the tissue contact apertures 27 can be varied according to individual needs. However, greater tissue contact across the device will promote better adhesion, drainage, and wound closure. Therefore, it is preferred that at least about 50%, 60%, or 70%, and preferably about 75-80% of the total surface area (one side) of the drain device remains open in the form of tissue contact apertures. The distribution and spacing of tissue contact apertures can be varied as desired, and the apertures can be the same, similar, or different in shape, size, and distribution across the device. For example, the apertures can be distributed with an average center-to-center spacing in the range of about 2 mm to about 20 mm or more, and the average individual aperture surface area can be in the range from about 1 mm$^2$ to about 5 cm$^2$. In a preferred embodiment, the apertures have about 1 cm$^2$ average surface area, and their number or their collective surface area become progressively larger from the proximal end of the drain device (i.e., near the exit point from the body) toward the distal end of the device (deep within the wound or seroma), so that tissue adhesion and wound closure progress from deep within the wound towards the surface of the body.

Figure 6A:
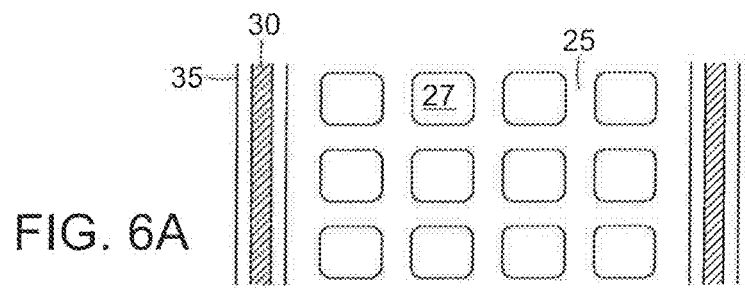
FIGS. 6A-C show illustrations of embodiments of an adhesion matrix having different types of tissue contact apertures.
Figure 6B:
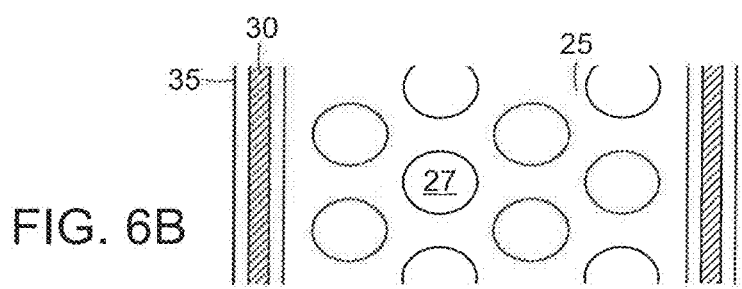
Figure 6C:
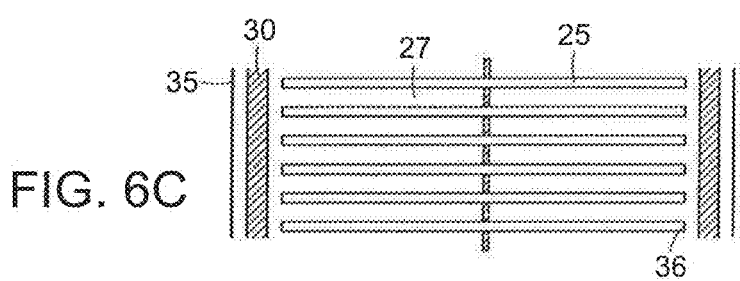
Figure 6D:
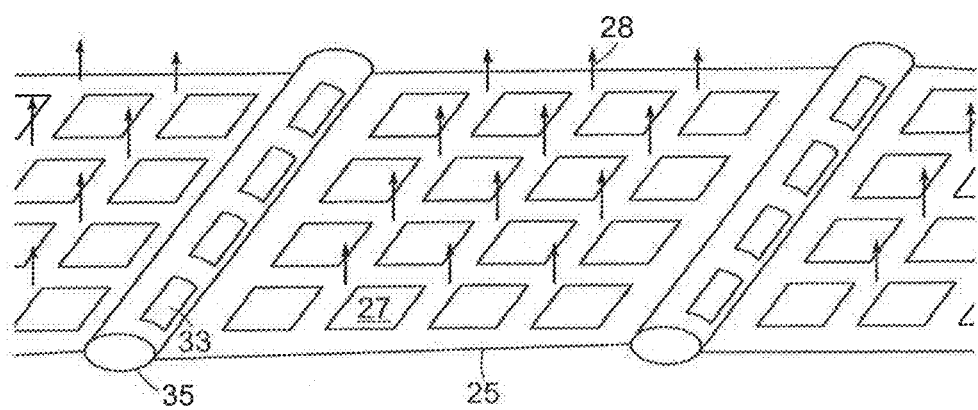
FIG. 6D is an illustration of an adhesion matrix embodiment possessing tissue anchors on its surface.
Figure 6E:
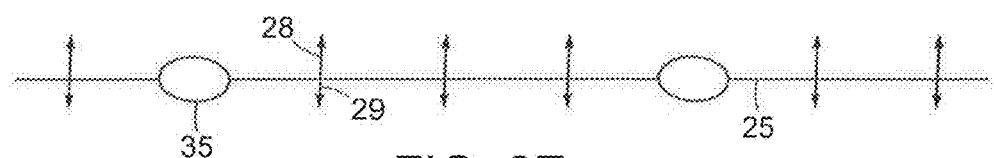
FIG. 6E shows a cross-sectional view of the adhesion matrix of FIG. 6D.

FIGS. 6A-E show several embodiments of the adhesion matrix. A portion of the adhesion matrix 25 between two neighboring drain tubes 30 and drain channels 35 is shown. The embodiment shown in FIG. 6A has a regular arrangement of rectangular apertures 27 to allow tissue contact through the device. Circular apertures are shown in FIG. 6B. The embodiment of FIG. 6C includes apertures 27 that are formed into lateral channels. Fluid flows laterally through these channels toward openings 36 in the drain tube channels, drawn by the reduced pressure in the drain tubes. As shown in FIGS. 6D and 6E, the surfaces of the adhesion matrix, including the drain channels, can be endowed with an array of hooks or barbs to promote anchoring of the device to adjacent tissues. In the embodiment shown in FIG. 6E, the hooks on the upper side 28 are longer than the hooks on the lower side 29. This arrangement can be used where the tissues on either side of the device are of different density. For example, longer hooks such as about 1.5 to about 3 mm in length are preferred for less dense tissue, such as subcutaneous fat tissue, whereas shorter hooks such as about 0.5 to about 1.5 mm in length are preferred for denser tissues such as fascia and muscle.

The adhesion matrix, including any drain tube channels and hooks or barbs, can be fabricated from a biodegradable polymer material, as these structures are intended to remain in place in the patient's body after removal of the drain tubes, so as not to disrupt the healing process. Examples of suitable biodegradable or resorbable materials include Vicryl (polyglycolic acid), Monocryl (glycolic acid-ε-caprolactone copolymer), PDS (polydioxanone, PDO), PLA (polylactic acid, polylactide), PLLA (poly-L-lactic acid), PDLA (poly-D-lactic acid), PGA (polyglycolic acid, polyglycolide), PLGA (poly(lactic-co-glycolic acid)), PHB (polyhydroxybutyrate), and PCL (polycaprolactone). In a preferred embodiment, the adhesion matrix, including any drain tube channels, is formed of an open network of polymer chains that has sufficient porosity to allow infiltration by cells and fluid flow across the material. Cellular infiltration can promote tissue adhesion and the biodegradation of the polymer after the wound has healed. In some embodiments, the adhesion matrix including any drain tube channels is permeable to seroma fluid but not permeable to cells. In other embodiments, the adhesion matrix, including any drain tube channels, is permeable to fluid and electrolytes but is impermeable to proteins. The permeability properties of the matrix polymer material that makes up the basic substrate of the matrix can be the same or different compared to the material that makes up the drain tube channels. In a preferred embodiment, the polymer chains, or fibers composed of polymer chains, of the adhesion matrix are aligned along an axis substantially perpendicular to the axes of the nearest drain tubes. This alignment pattern promotes the flow of fluid through or along the surface of the adhesion matrix towards the drain tubes.

The adhesion matrix, and thus the overall drain device, can have any form suitable for insertion into the wound or seroma where it is to be inserted. Generally, the form is that of a thin sheet or flexible planar mesh having an essentially rectangular shape. However, the shape can be rounded, circular, elliptical, oval, or irregular. Preferably the corners are rounded so as to minimize mechanical irritation of surrounding tissues. The size of the device is also determined by the particular use and anatomy of the patient. For example, the adhesion matrix can have an overall width and length in the range from about 2 cm to 25 cm, such as about 10 cm×12 cm or about 20 cm×25 cm. The thickness of the adhesion matrix can be from about 0.5 mm to about 1 cm; where the sheet of material is preferably less than 5 mm in thickness and preferably the adhesion matrix is about 1-2 mm thick. The thickness of the entire drain device, including the sheet of the adhesion matrix, drain tubes, and any hooks or glue pads is about 5 mm or less, 10 mm or less, or about 5-10 mm.

The adhesion matrix can be coated with an adhesive material such as surgical glue either in addition to or instead of using hook or barb structures that stabilize tissue layers on either side of the drain device. Any type of surgical adhesive suitable for use within the body can be used, including polyethylene glycol polymers, adhesive proteins, gelatin-thrombin mixtures, albumin-glutaraldehyde, and fibrin-based sealants. Cyanoacrylates are to be avoided, as they cause inflammation if used internally. An adhesive coating can be placed on one or both surfaces of the adhesion matrix. Adhesive coatings can be applied to the device prior to its placement in a patient, i.e., as part of the device fabrication process. An adhesive coating can cover all or a portion of a surface of the device. A surgical adhesive can be used in the form of a fibrous mat or pad that is soaked or coated with an adhesive composition. The mat or pad is preferably fabricated from a biodegradable polymer, such as the type used to prepare the adhesion matrix. One or more layers of adhesive material can be placed between the device and surrounding tissue at the time of placement in the patient.

Figure 7A:
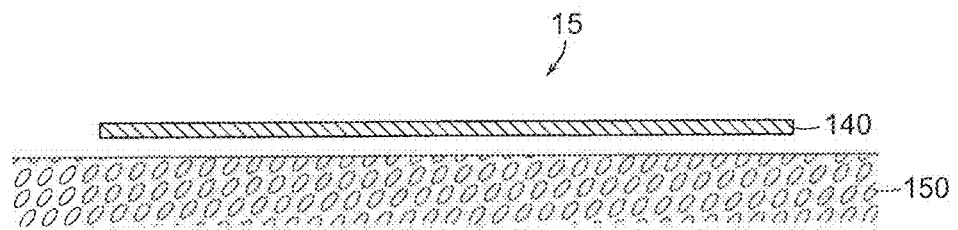
FIGS. 7A-7D are cross-sectional illustrations of different embodiments of the drain device positioned within a wound or seroma wherein these embodiments include one or more layers of adhesive and/or tissue anchor arrays.
Figure 7B:
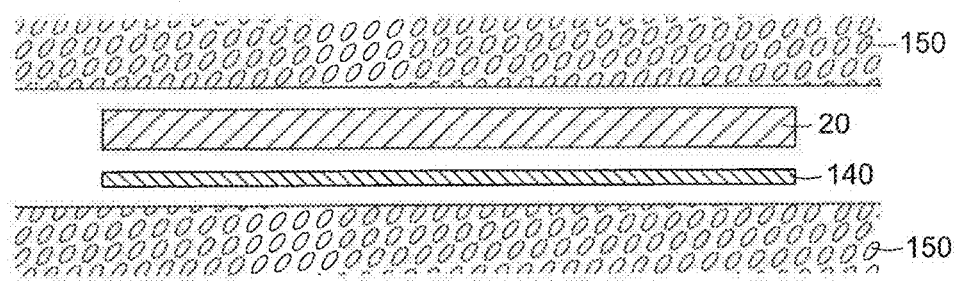
Figure 7C:
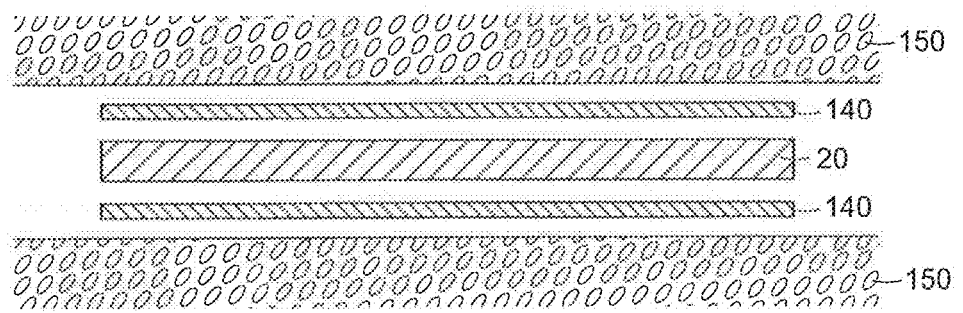
Figure 7D:
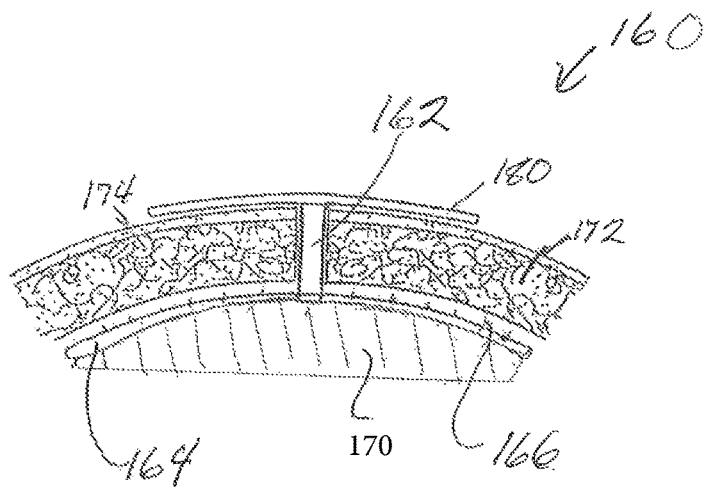

FIGS. 7A-7C illustrate the placement of supplemental adhesive layers with the drainage device. In FIG. 7A, adhesive layer or pad 140 has been placed into a wound or seroma adjacent to exposed tissue 150. In FIG. 7B, drainage device 20 has been placed onto the adhesive layer as shown in FIG. 7A, and the wound then closed and vacuum applied, so that the device-adhesive pad sandwich is surrounded by tissue 150. FIG. 7C depicts the structure obtained if a second adhesive pad or layer 140 is added adjacent to the drainage device on the opposite side of the first adhesive layer. Shown in FIG. 7D is a drainage device 160 that has a composite structure in which a first drainage element 164 as described herein extends orthogonally from a second element 162. The first drainage element can have tissue anchor elements 166 on one or both sides that engage tissue regions 170, 172 on different sides of the first element. Second element 162 can comprise a drainage device with detachable drain tubes as described herein, or in another embodiment, can comprise a double-sided tissue anchor device. In this embodiment, since the tissue 172 is the same (such as fat tissue 172 underneath dermal layer 174) on both sides of tissue anchor device 162, the anchor elements on both sides can have the same size and shape. Such adipose tissue can comprise cells connected by fibrous tissue. The cells can range in size from 1 mm$^2$ or 5 mm$^2$, so that the anchor elements can be spaced and sized to match the cellular features or the tissue into which they are inserted. In the event that elements 162, 164 are to be connected to a negative pressure source as described herein, layer 180 serves to seal the wound and provides a port to connect drainage tubes, such as those shown in FIGS. 4-6 and 9. Note that the tubes can extend through both elements 162, 164. Anchor device 162, 164 can comprise bioabsorable material which remain in place after wound closure until fully absorbed. The elements 162, 164 can utilize the same or different size apertures in a range of 1 mm$^2$ or 5 mm$^2$ or can comprise less than 1 mm$^2$ in size.

Figure 8:
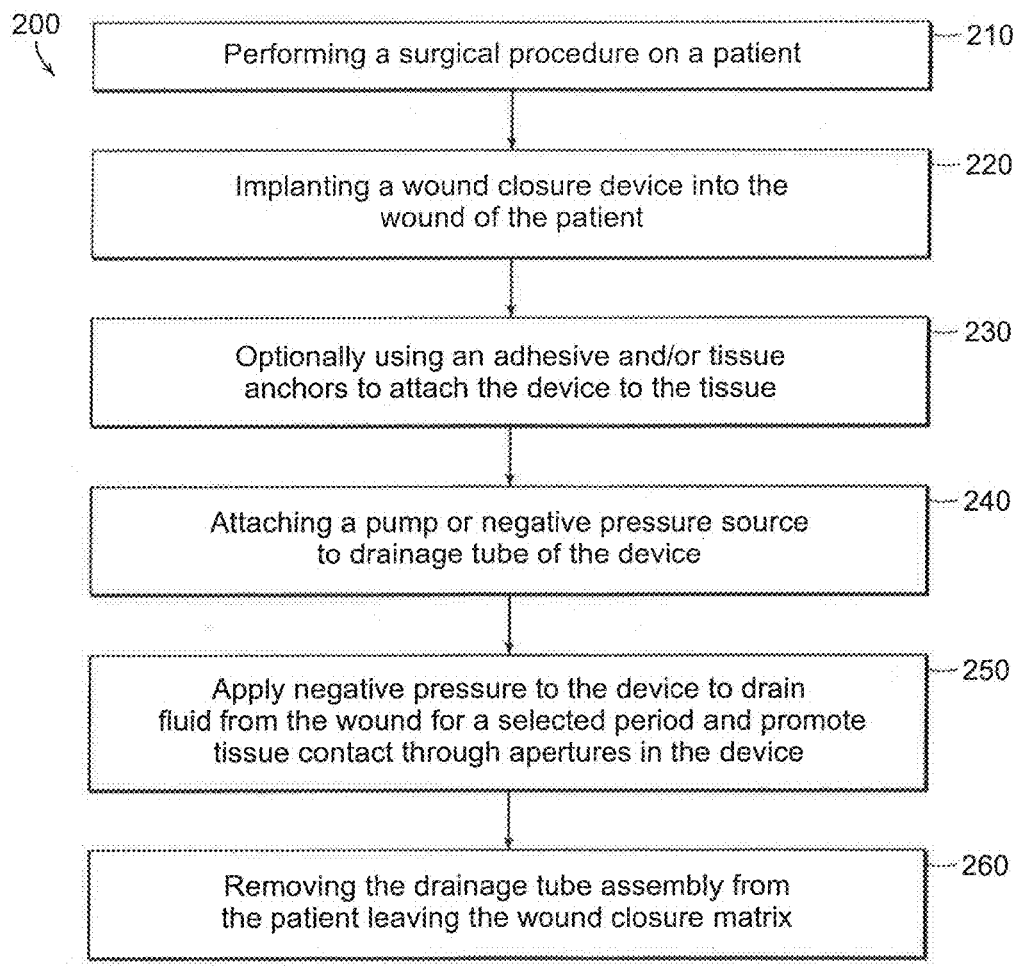
FIG. 8 illustrates a process sequence of performing wound closure treatment in accordance with preferred embodiments of the invention.

The invention also provides a method for treating or preventing a seroma as illustrated in FIG. 8. The method also can be used to promote wound closure after surgery 210, to prevent infection after surgery, and to improve the strength and/or cosmetic appearance of a surgical wound after it has fully healed. A drain device according to the invention is positioned into a surgical wound 220, such as a wound following abdominal flap surgery. The device has been sterilized prior to placement within the wound. Optionally, one or more layers of surgical adhesive is placed on one or both sides of the device, interfacing between the device and surrounding tissue 230. If the device includes hooks or barbs on one or both sides, pressure is applied to the surface of the device in order to set the hooks or barbs into the surrounding tissue. The wound is then partially surgically closed at the surface, leaving a single tube exiting the wound. The tube is then attached to a vacuum source 240, and vacuum is applied 250 so as to initiate drainage through the device. The rate of drainage is controlled by the level of vacuum applied. The amount of vacuum is sufficient to promote drainage without causing damage to the tissues surrounding the implanted device. For example, the vacuum can be in the range from about 75 to 250 mm Hg. After the rate of fluid drainage has decreased to acceptable levels, the vacuum is removed and the drain tubes are removed 260 by slowly pulling them out through the remaining wound opening, which is subsequently closed. The adhesion matrix remains in the patient and is biodegraded and absorbed over a period of weeks to months.

Figure 9A:
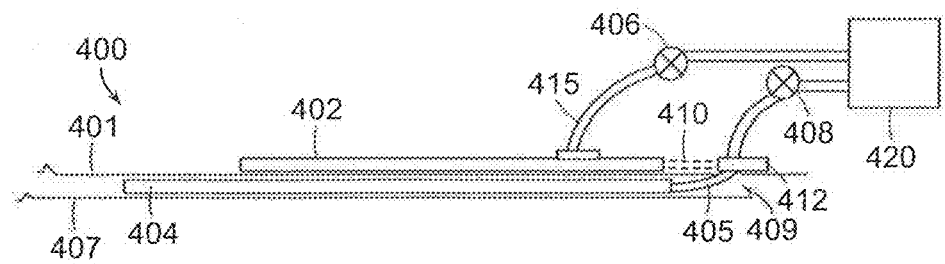
FIG. 9A illustrates a wound drainage and wound dressing system in which the wound dressing does not overlie the drainage exit site.
Figure 9B:
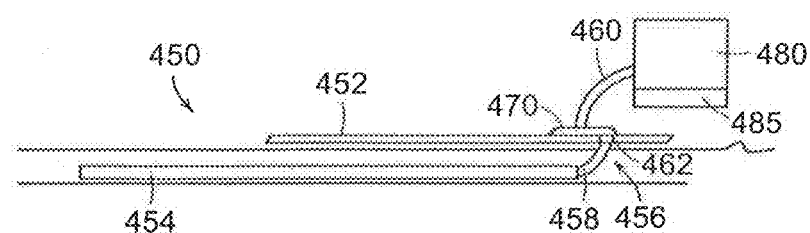
FIG. 9B illustrates a wound drainage and dressing system in which the wound dressing does not overlies the drainage exit site.

Illustrated in connection with FIGS. 9A and 9B are uses of a wound dressing in combination with the adhesion matrix or mesh device and a negative pressure drainage system. After placement of the matrix 404, as described in detail herein, the drainage tubing 405 extends through an exit site 409 of the skin 401 of a patient. The wound can frequently require the use of a wound dressing 402 that is placed externally on the skin of a patient. The wound dressing can either overlie the exit site 456 as shown in FIG. 9B, or the wound dressing can be placed laterally (or non-overlying) from the exit site 409 as shown in FIG. 9A. The tubing 405 can either connect directly to the pump 420, or can utilize a connector or manifold 412 positioned on or above the skin 401, which can be connected to the pump 420. A valve 408 can be used to control the application of negative pressure. A flow meter can be included at the connector or manifold 412 or at the valve 408 to measure the fluid removal rate and total amount of fluid removed. A quantitative measure of the fluid removed can thereby be measured and recorded. Other diagnostic measurement devices, such as ultrasound, can also be used to measure the amount and location of fluid or seromas within the wound. This information can be used to adjust the amount and distribution of negative pressure applied within both the wound using drainage system 404, 454 and the wound dressing 402, 452.

Negative pressure can be applied to the wound dressing 402 through separate tube 415 that can be attached to the same pump 420 as the drainage system or a second pump. A valve 406 can be used to regulate pressure to the wound dressing. In the embodiment of FIG. 9B, tube or tubes 458 can exit the wound and attach at connector 462 to the underside of the dressing 452. A manifold 470 can control the distribution of negative pressure to both the dressing 452 and the drainage device 454 using passive or active flow control elements. The manifold can be attached using a single tube 460 to pump 480. The pump 420, 480 can be operated by hand or electronically. The pump can have internal electronic control, memory and display features 485 to control system operation and record patient data.

Figure 10A:
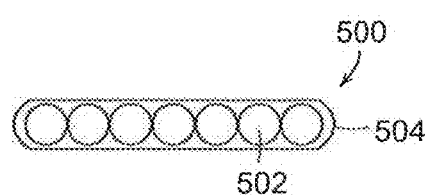
FIGS. 10A and 10B illustrate cross-sectional view of drainage exit tube assemblies that can be used in preferred embodiments of the invention.
Figure 10B:
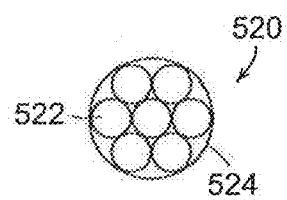

Shown in FIGS. 10A and 10B are preferred embodiments of drainage tube assemblies that can be used in conjunction with the invention. The drainage tubing 405, 458 preferably exits the wound as a single tube or as a cluster of tubes within an outer tube. The outer tube 504 can either be a flattened shape 500 of a plurality of three or more tubes 502 arranged in line as shown in FIG. 10A, or can be circular 520 with drainage tubes 522 extending within outer tubes 522 to the pump or connector. In certain applications, it may be advantageous to remove the tubes separately at different times from the drainage system as certain regions may drain more quickly. However, for many wounds it is useful to simultaneously remove all drainage tubes from the wound.

Figure 11:
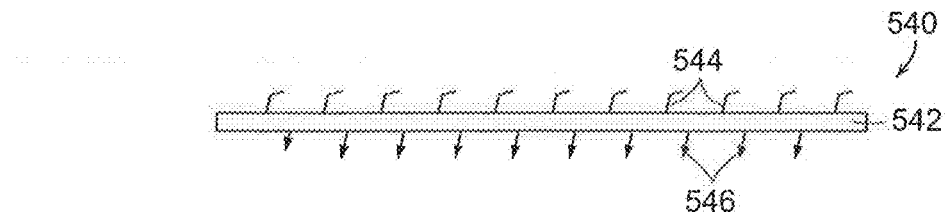
FIG. 11 is a side view of a tissue anchoring mesh in accordance with preferred embodiments of the invention.

Shown in FIG. 11 is a side view of an adhesion matrix or mesh 540 used in preferred embodiments of the invention. It can frequently be useful to employ such a mesh to facilitate wound adhesion and healing using an absorbable material that can adhere on both sides to tissues within a wound. Frequently, these tissues are of different types on opposite sides of the mesh. Thus, the mesh can include a conformable layer 542 having tissue anchors 544, 546 on both sides. However, as one side may be used to attach to the fatty or adipose tissue on the underside of a flap of skin, the first plurality of tissue anchors 544 has a shape and rigidity suitable for attaching to adipose tissue. The second plurality of tissue anchors can be shaped and sized to attach to less compliant tissues such as fascia or muscle. More rigid hooks or barbs are needed to enable this attachment.

Figure 12:
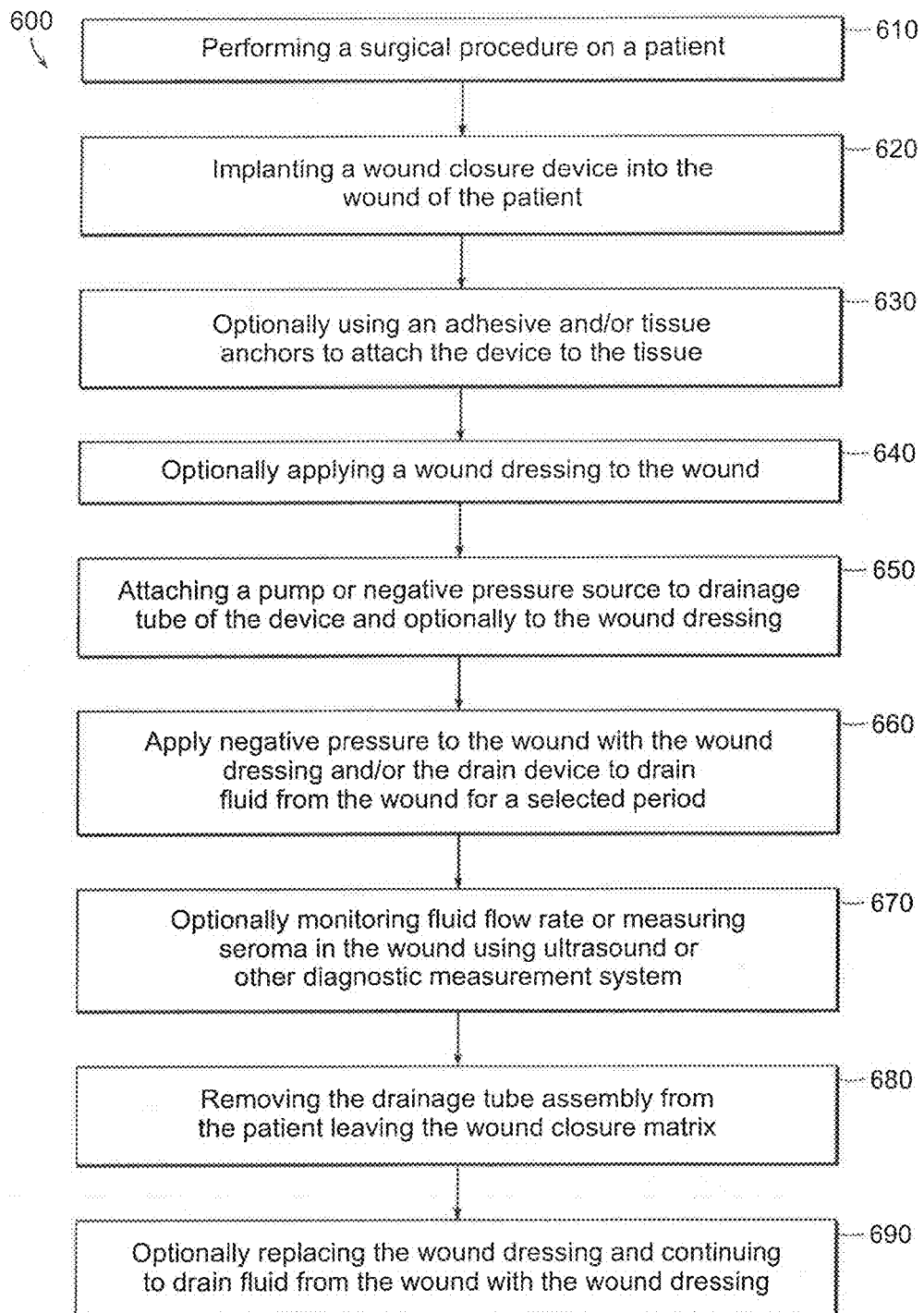
FIG. 12 is a process flow diagram illustrating a method of using a wound dressing and drainage system in accordance with preferred embodiments of the invention.

As illustrated in FIG. 11, the anchor elements 544 on a first side of the layer 542 can be oriented at an oblique angle that is less than 90 degrees relative to the first side and the anchor elements 546 can also be oriented at an oblique angle that is less than 90 degrees from the second side of the layer 542. Thus, the anchor elements 544, 546 can be angled in opposite directions, as shown in FIG. 11, so that if the tissue regions are under tension to apply forces to the layer 542 in opposite directions, these forces will tend to cause the tissue to engage the anchor elements. Shown in FIG. 12 is a sequence of steps in a method 600 of applying a drainage and wound dressing system in accordance with the invention. After performing a procedure 610 on a patient, a wound closure device is inserted 620 into the wound of a patient. This can be a combination of elements, such as meshes as shown in FIG. 11 in certain regions of the wound, and a drainage and mesh system as described generally herein in regions of the wound requiring drainage of fluid. This can also include the user 630 of adhesives and/or tissue anchors to enable more direct contact of tissues through the mesh and thereby improve the rate of healing. A wound dressing can also be applied 640 to the wound as described herein. A pump can then be attached 650 to the drainage system and/or the wound dressing and a negative pressure can be applied 660 to one or both elements to drain fluid and promote contact between tissues through the implanted mesh or matrix. The flow rate of fluid through each tube can be measured and recorded and the presence of fluid can be monitored 670 by ultrasound or other systems. The drainage tubing can be removed 680 when the drainage rate diminishes. The wound dressing can be replaced 690 as needed and can continue to be used to drain 690 the wound.

Figure 13:
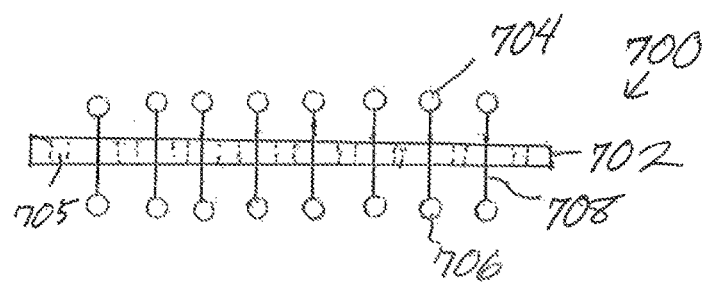
FIG. 13 illustrates a composite tissue anchor mesh in accordance with a preferred embodiment of the invention.

A tissue anchor device 700 shown in FIG. 13 has a composite structure in which the anchor elements include posts 708 that extend through the mesh 702 which can also include pores 705 that provide tissue contact across the mesh. The posts have anchor tips 704, 706 on opposite ends that penetrate tissue. The posts can be more rigid than the mesh so that a user can manually press the device 700 relative to the tissue to insert the tips 704, 706 into the tissue. The posts 708 are attached to a flexible mesh that allows for rotation of the posts relative to the mesh. The posts can also be attached at oblique angles relative to the mesh.

Figure 14:
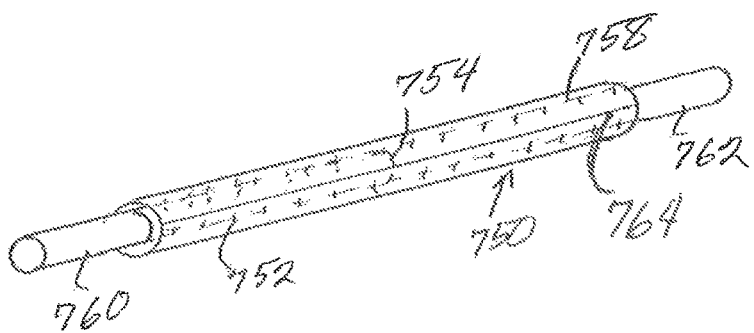
FIG. 14 illustrates the insertion of a tubular tissue anchor device into a tissue surface in accordance with preferred embodiments of the invention.

Shown in FIG. 14 is a double-sided tissue mesh in which one side has a two-dimensional array of tissue anchors distributed on a first side of the mesh. This comprises an implant material which can be used to attach an organ (such as the lung or colon) to adjoining tissue, or as shown in FIG. 14, where the mesh has a tubular shape 750 with anchor elements 752 on the internal surface. The device can have a smooth external surface 758 that can slide with respect to adjoining tissue structures. In this example, a tendon or nerve 760, 762 can be surrounded by the tubular body in which the internal surface elements 752 are inserted into the tissue on the two portions of the nerve or tendon abutting an injured region 754. Thus, severed nerves or tendons can be reattached using the present device. The tubular body can have a longitudinal slit so that it can be wrapped around the tendon or nerve after positioning by the surgeon.

The tissue anchor elements can have different geometries depending on the type of tissue being grasped. The anchor elements can be single fiber strands with curved ends, sharpened ends, mushroom or ball shaped ends. The anchor elements can have different lengths (from 100 microns to 5 mm) on different sides or regions of the mesh.

As seen in FIG. 15, the individual tissue anchor elements can comprise a plurality of barbs, hooks or tongs that can penetrate into the tissue at different depths. In this example, hook element 830 is outside the tissue surface but has grasped fibrous tissue 832 at the surface. Deeper hooks 840, 842 can grasp fibrous tissue below the tissue surface that thereof distribute the grasping force over a larger volume of the tissue. Note that elements 830, 840, 842 can have elastic behavior that allows them to bend and release from the tissue under sufficient force. The mesh is pressed against the tissue surface causing the anchor elements to penetrate cells without damaging the fibrous tissue strands of connective tissue. The cells can have differing diameters so that the sizes of the anchor elements and spacing between these elements can be selected based on the tissue involved.

While this invention has been particularly shown and described with references to preferred embodiments thereof, it will be understood by those skilled in the art that various changes in form and/or details therein and equivalents thereof may be made without departing from the spirit and scope of the invention as set forth by the appended claims.

What is claimed is:

1. A negative pressure surgical drain device comprising a plurality of drain tubes positioned in contact with a surface of an adhesion matrix, the adhesion matrix comprising a layer of porous biodegradable material having a wound conforming shape and comprising a plurality of spaced apertures formed through the layer of the adhesion matrix, the apertures being configured to allow tissue contact through the layer of the adhesion matrix upon implantation into an open wound such that a first tissue surface on a first side of the layer of the adhesion matrix can contact a second tissue surface on a second side of the layer of the adhesion matrix through the plurality of apertures during application of negative pressure to the wound, the drain tubes being positionable at tube receiving regions of the layer of the adhesion matrix between the spaced apertures and wherein the drain tubes are configured to be removed from contact with the surface of the layer of the adhesion matrix after application of negative pressure to the adhesion matrix, the adhesion matrix being configured to remain in the wound upon removal of the drain tubes from the wound.

2. The device of claim 1 wherein the adhesion matrix further comprises an adhesive that bonds the adhesion matrix to a tissue surface of the wound.

3. The device of claim 1 wherein the adhesion matrix further comprises a tissue anchor that attaches the adhesion matrix to a tissue surface of the wound.

4. The device of claim 1 wherein the plurality of drain tubes comprises at least three tubes connected to a manifold wherein each tube has a lumen to transport fluid.

5. The device of claim 1 wherein the adhesion matrix comprises a flexible planar mesh having a thickness of less than 2 mm.

6. A system for surgical wound drainage, the system comprising the drain device of claim 1, a vacuum source, and a tube connecting the vacuum source to the drain tubes of said drain device such that a negative pressure is applied to the wound.

7. The device of claim 1 wherein the adhesion matrix comprises a polymer mesh having a first plurality of tissue anchors on a first side surface and a second plurality of tissue anchors on a second side surface.

8. The device of claim 1 wherein each drain tube extends from a wound entry site at a proximal portion to a distal end positionable within a wound.

9. The system of claim 6 wherein the drain device further comprises a wound dressing.

10. The system of claim 9 wherein the wound dressing is coupled to a pump.

11. The system of claim 9 wherein the wound dressing overlies a drain tube exit site.

12. The system of claim 6 further comprising a flow regulation system that regulates flow from the drain tubes.

13. The device of claim 1 wherein the apertures have varying sizes.

14. The device of claim 1 wherein a total area of the apertures is at least 50 percent of a surface area of the matrix.

15. The device of claim 7 wherein the first plurality of tissue anchors are more rigid than the second plurality of tissue anchors.

16. The device of claim 4 wherein the manifold is connectable to a negative pressure source.

17. The device of claim 1 wherein the drain tubes are positioned in a spaced array emanating along different radial directions from an edge of the matrix.

18. The device of claim 1 wherein the drain tubes are positioned in drain channels of the matrix.

19. The device of claim 1 wherein the apertures are positioned to promote flow to the drain tubes.

20. A negative pressure surgical drain device comprising a matrix having a wound conforming shape for abdominal flap surgery, the matrix comprising a layer of porous biodegradable material having a plurality of spaced apart apertures formed through the layer and configured to allow tissue contact through the matrix upon placement into an abdominal wound such that a first tissue surface within the abdominal wound on a first side of the matrix can contact a second tissue surface on a tissue flap of the abdominal wound on a second side of the matrix through the plurality of apertures during application of negative pressure to the wound, the matrix further comprising tube receiving regions on a surface of the matrix layer adapted to receive a plurality of drain tubes connectable to a negative pressure source, the tube receiving regions extending across the surface of the matrix and wherein one or more of the plurality of apertures are located between the tube receiving regions and are configured such that the drain tubes can be removed from the wound after the application of negative pressure to the wound such that the matrix remains in the wound after wound closure.

21. The device of claim 20 wherein the matrix further comprises an adhesive.

22. The device of claim 20 wherein the matrix further comprises a tissue anchor.

23. The device of claim 20 wherein the plurality of drain tubes comprises at least three tubes connected to a manifold.

24. The device of claim 20 wherein the matrix layer comprises a sheet having a thickness of less than 2 mm.

25. The device of claim 20 wherein each of the plurality of apertures have an area in a range of 1 mm$^2$ to 5 cm$^2$.

26. The device of claim 20 wherein a total area of the apertures is at least 50 % of the surface area of the matrix.

27. The device of claim 20 further comprising a first plurality of tissue anchors on the first side of the matrix and a second plurality of tissue anchors on the second side of the matrix, the first plurality of tissue anchors adapted to attach to adipose tissue and the second plurality of tissue anchors adapted to attach to fascia and/or muscle tissue.

28. The device of claim 7, wherein each of the first side surface and the second side surface comprise from 1 to 10 tissue anchors per square millimeter.

29. The device of claim 7, wherein the first plurality of tissue anchors and the second plurality of tissue anchors comprise anchors of different lengths.

30. The device of claim 7, wherein the first plurality of tissue anchors and the second plurality of tissue anchors comprises single fiber strands having one of curved ends, sharpened ends, mushroom ends, or ball-shaped ends.

31. The device of claim 7, wherein the first plurality of tissue anchors and the second plurality of tissue anchors comprises tips or ends that are shaped to promote adhesion.

32. The device of claim 7, wherein the first plurality of tissue anchors comprise a first end of a plurality of posts and the second plurality of tissue anchors comprise a second end of the plurality of posts, the first end and the second end of the plurality of posts having anchor tips that can penetrate tissue.

33. The device of claim 32, wherein the plurality of posts can rotate relative to the polymer mesh.

34. The device of claim 7, wherein a first portion of the first plurality of tissue anchors can penetrate into a tissue more deeply than a second portion of the first plurality of tissue anchors.

35. The device of claim 7, wherein the first plurality of tissue anchors or the second plurality of tissue anchors are elastic such that they bend and release from a tissue under sufficient force.

36. A negative pressure surgical drain device comprising:
   a matrix having a wound conforming shape and a drain channel; and
   a drainage element positioned within the drain channel wherein the matrix comprises a layer of porous biodegradable polymer and a plurality of spaced apertures formed through the layer and configured to allow tissue contact through the matrix, the plurality of spaced apertures having a total area of at least 50 percent of an area of a first side of the matrix such that a first tissue surface on the first side of the matrix can contact a second tissue surface on a second side of the matrix through the plurality of spaced apertures during application of negative pressure to the matrix, the drainage element being connectable to a negative pressure source and configured to be removed from the drain channel that is positioned between apertures of the matrix, the matrix being configured to remain in the wound upon removal of the drainage element from the drain channel.

37. The device of claim 36, wherein the drainage element comprises one or more drain tubes.

38. The device of claim 37, further comprising a sealing layer to seal a wound and provide a port to connect the plurality of drain tubes.

39. The device of claim 36, wherein a first side of the matrix comprises a plurality of tissue anchors.

40. The device of claim 36, wherein each of the plurality of apertures have an area in a range of 1 mm$^2$ to 5 cm$^2$.

41. The device of claim 36, wherein each of the plurality of apertures have an area less than 1 mm$^2$.

42. The device of claim 36, further comprising an adhesive.

* * * * *